United States Patent
Schmid et al.

(10) Patent No.: US 7,455,795 B2
(45) Date of Patent: Nov. 25, 2008

(54) CHARGE TRANSFER COMPLEXES INCLUDING AN ELECTRON DONOR AND AN ELECTRON ACCEPTOR AS BASIS OF RESISTIVE MEMORIES

(75) Inventors: Guenter Schmid, Hemhofen (DE); Peter Baeuerle, Elchingen (DE); Elena Mean-Osteritz, Elchingen (DE); Marcus Halik, Erlangen (DE); Hagen Klauk, Erlangen (DE)

(73) Assignee: Infineon Technologies AG, Munich (DE)

( * ) Notice: Subject to any disclaimer, the term of this patent is extended or adjusted under 35 U.S.C. 154(b) by 486 days.

(21) Appl. No.: 11/023,368

(22) Filed: Dec. 29, 2004

(65) Prior Publication Data

US 2005/0198462 A1 Sep. 8, 2005

(30) Foreign Application Priority Data

Dec. 30, 2003 (DE) ................................ 103 61 713

(51) Int. Cl.
*H01L 35/24* (2006.01)
*H01B 1/12* (2006.01)
*G11C 11/00* (2006.01)
*G06F 12/08* (2006.01)

(52) U.S. Cl. .................. 252/519.33; 252/510; 252/511; 252/582; 252/501.1; 257/40; 257/184; 257/295; 365/148; 438/99; 711/200

(58) Field of Classification Search ............... 252/501.1, 252/582; 365/145, 151, 153; 257/40, 184
See application file for complete search history.

(56) References Cited

U.S. PATENT DOCUMENTS

| | | | | |
|---|---|---|---|---|
| 4,122,541 | A * | 10/1978 | Uchida | 365/154 |
| 5,454,880 | A | 10/1995 | Sariciftci et al. | |
| 5,505,879 | A | 4/1996 | Wang | |
| 6,212,093 | B1 * | 4/2001 | Lindsey | 365/151 |
| 6,215,130 | B1 * | 4/2001 | Dodabalapur | 257/67 |
| 6,265,243 | B1 * | 7/2001 | Katz et al. | 438/99 |
| 6,312,304 | B1 * | 11/2001 | Duthaler et al. | 445/24 |
| 6,483,099 | B1 * | 11/2002 | Yu et al. | 250/214.1 |
| 6,872,969 | B2 * | 3/2005 | Redecker | 257/40 |
| 6,987,689 | B2 * | 1/2006 | Bozano et al. | 365/148 |
| 2005/0224922 | A1 * | 10/2005 | Lyons | 257/642 |

FOREIGN PATENT DOCUMENTS

| | | |
|---|---|---|
| EP | 1 209 708 A1 | 5/2002 |
| WO | WO 99/09603 A1 | 2/1999 |
| WO | WO 03/079003 A2 | 9/2003 |

OTHER PUBLICATIONS

Kromer et al, "Homologus series of regioregular alkylsubsituted oligothiophenes upto an 11-mer," Tetrahedron, 2001, 57, 3785-3794.*

* cited by examiner

*Primary Examiner*—Stanley Silverman
*Assistant Examiner*—Kallambella Vijayakumar
(74) *Attorney, Agent, or Firm*—Edell, Shapiro & Finnan, LLC

(57) ABSTRACT

Materials are described for producing memory cells which have a size in the nanometer range and include a CT complex located between two electrodes. The CT complex includes thiophene derivatives, pyrrole derivatives or phthalocyanines together with naphthalenetetracarboxylic acid, dianhydrides, diamides, fullerenes or perylene compounds.

4 Claims, 3 Drawing Sheets

CHARGE TRANSFER COMPLEXES INCLUDING AN ELECTRON DONOR AND AN ELECTRON ACCEPTOR AS BASIS OF RESISTIVE MEMORIES

CROSS REFERENCE TO RELATED APPLICATIONS

This application claims priority under 35 U.S.C. § 119 to German Application No. DE 103 61 713.2, filed on Dec. 30, 2003, and titled "Charge Transfer Complexes Comprising an Electron Donor and an Electron Acceptor as Basis of Resistive Memories," the entire contents of which are hereby incorporated by reference.

FIELD OF THE INVENTION

The invention relates to a resisitive memory cell comprising a charge transfer complex comprising an electron donor and an electron acceptor and a process for producing the same.

BACKGROUND

One of the important aspirations in the further development of modern memory technologies is to increase the integration density; consequently, achieving a reduction in the structural sizes of the memory cells on which the memory devices are based is of great importance. Conventional memory cells are produced by lithographic techniques. To reduce the memory cell size, ever shorter wavelengths are being used for illumination in such lithographic techniques in order to improve the resolution of the lithographic techniques. To further advance this technology, new resist materials continually have to be developed for this purpose and the existing techniques have to be improved. With this in mind, it can be foreseen that lithographic techniques will soon come up against their practical limits. For this reason, new methods which make it possible to reduce the size of electronic components without having to use conventional lithographic techniques are being developed. These are intended to make viable electronic components which have a size in the nanometer range and are therefore several orders of magnitude smaller than the electronic components which can be produced by present lithographic techniques.

A further aspect of increasing the memory available per unit area of a memory device is the provision of memory cells which allow higher quality information units in the form of multiple states at one location in the sense of a multilevel information storage.

In recent years, a number of microelectronic elements which have a size of a few nanometers have been described. These elements are referred to as nanoelements, and the technology for producing them is referred to as nanotechnology. The proposed elements generally have a molecular layer (monolayer) located between two electrodes. The monolayers are preferably formed by self-organization on a suitable substrate. Such elements can, in the ideal case, be reduced to sizes in the molecular range from about 0.5 to 5 nm. In general, a number of individual molecules limited by the electrode area (e.g. 10 nm×10 nm) (e.g. 100, so that the density is about 1 molecule per 1 $nm^2$) is used for producing a memory function so as to increase the statistical certainty. These molecules are preferably located in a passive matrix or in a molecular assembly, with an assembly of molecules forming the memory function at each intersection point of the passive matrix.

In "A nanometer scale electronic switch consisting of a metal cluster and redox-addressable groups," Nature, vol. 408, 2000, pages 67 to 69, Gittins et al. describe gold nanoclusters which have a size of a few nanometers and are functionalized with polymethylene chains. The chains bear a redox-active bipyridinium radical, so that the properties of the gold cluster can be altered as a function of the oxidation state of the bipyridinium radical. Gittins et al. describe the switching behavior of the gold nanoparticles by scanning microscopy (STM) and show that such a molecular switch has various, distinguishable states. The disadvantage of this concept is that the free radical formed by uptake of an electron into the bipyridinium radical is delocalized over only a few atoms and is therefore sensitive to oxygen or other oxidizing agents. This makes the concept described in Gittins et al. unsuitable for use in a microelectronic component.

Collier et al., in "Electronically configurable molecular-based logic gates," Science, vol. 285, 1999, pages 391-393, describe molecular switches which can be used as logic gates. The molecular switches described in Collier et al. can be used as a Programmable Read Only Memory (PROM) cell. The molecular switches described in Collier et al. have a monolayer of mechanically interlocked molecular units (rotaxanes). The molecular units consist of a crown ether which is arranged around a chain bearing two bipyridinium radicals. In this structure, too, the free radical is delocalized over only a few atoms and is therefore very sensitive to oxygen. In addition, the switching process is not reversible.

Lee et al. describe in "Fabrication approach for molecular memory arrays," Applied Physics Letters, vol. 82, 2003, page 645-647, molecular wires comprising phenylene-ethylene oligomers arranged as a monolayer between two palladium nanowires.

U.S. Pat. No. 5,505,879 describes charge transfer complexes between fullerenes and particular electron donors in general. The molecular ratio between the electron donors and the fullerenes is from 1:3 to 6:1, with the preferred ratio being from 1:1 to 3:1. The preferred electron donor is N,N-diethylaniline. The use of these complexes for producing semiconductor elements cannot be deduced from this prior art.

SUMMARY

The invention provides: a new way of using known materials for producing semiconductor elements so that the semiconductor elements can be scaled down to a size of a few nanometers; new materials which can be used as a basis of memory elements and in particular memory elements having a size of a few nanometers; non-volatile memory cells which can be scaled down to a size of a few nanometers and preferably operate according to the resistive principle, and also a process for producing them; and new non-volatile memory cells which can be used as multibit memories.

The invention provides a new way of using known materials for producing semiconductor elements so that the semiconductor elements can be scaled down to a size of a few nanometers by the use of oligomeric, polymeric or cyclic derivatives of the general formulae I or II

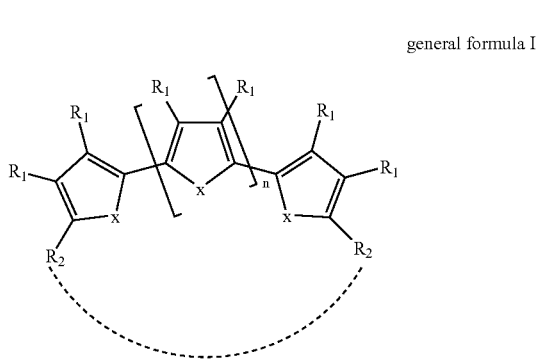

general formula I where:

n=1-8 when the radicals $R_2$ are not linked to form a ring and 1-100, preferably 6-30, when the radicals $R_2$ are linked to one another;

X=N or S;

the radicals $R_1$ are each, independently of one another, H or a linear or branched alkyl chain which has from 1-10 carbon atoms and may also be substituted by heteroatoms;

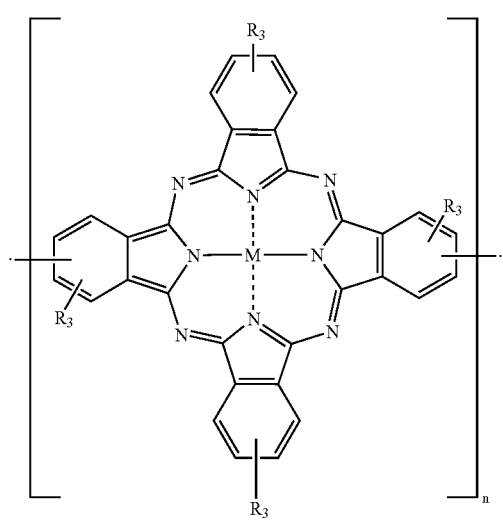

general formula II where n=1-5, preferably 1;

the radicals $R_3$ are each, independently of one another, H, a linear or branched alkyl chain which has from 1-10 carbon atoms and may be substituted by heteroatoms, or a halogen atom selected from the group consisting of F, Cl, Br or I;

M is a metal or a metal ion.

The compounds of the general formula I in which X=N are known. Possible syntheses are described, for example, in T. A. Skotheim, R. L. Elsenbaumer, J. R. Reynolds; Handbook of Conducting Polymers, Marcel Dekker, Inc., New York, Basle, Hong Kong, ISBN 0-8247-0050-3 (1998), pages 260-276; 423-424 and references cited therein (ibid, 1032ff, 1038ff).

The compounds of the general formula I in which X=S are described, for example, in E. Mena-Osteritz, P. Bäuerle, Adv. Mater. 2001, 13, 243-246 "Self-assembled Hexagonal Nanoarrays of Novel Macrocyclic Oligothiophene-Diacetylenes"; J. Krömer, I. Rios-Carreras, G. Fuhrmann, C. Mush, M. Wunderlin, T. Debaerdemaeker, E. Mena-Osteritz, P. Bäuerle, Angew. Chem. 2000, 112, 3623-3628 "Synthesis of the first Fully π-conjugated Macrocylic Oligothiophenes: Cyclo[n]thiophenes with tunable Cavities in the Nanometer Regime"; E. Mena-Osteritz, P. Bäuerle, Angew. Chem. 2000, 112, 2791-2796: "Two-dimensional Crystals of Self-organized Poly(3-alkylthiophene)s: Direct Visualization of Polymer Chain Conformations in Submolecular Resolution"; J. Krömer, P. Bäuerle, Tetrahedron 2001, 57, 3785-3794: "Homologous Series of Regioregularly Alkylsubstituted Oligothiophenes up to a 11-mer".

The compounds of the general formula II are likewise known and can be prepared by the methods described in T. A. Skotheim, R. L. Elsenbaumer, J. R. Reynolds; Handbook of Conducting Polymers, Marcel Dekker, Inc., New York, Basle, Hong Kong, ISBN 0-8247-0050-3 (1998), pages 381-407 (with references cited therein).

Preference is given to using the compounds of the general formula I in which X=S.

In a particular embodiment, $R_1$ is a t-butyl or i-propyl group.

Particular preference is given to oligothiophenes which can be linear or cyclic (n=1-20).

Among the compounds of the general formula II, particular mention may be made of the compounds in which n=1, $R_3$=F. The preferred metals (M) are Cu, Co and Zn. Particular preference is given to the 1,2,3,4,8,9,10,11,15,16,17,18,22,23,24,25-hexadecafluoro-29H, 31H-phthalocyanonecopper(II) complex.

The materials according to the invention can be used for microelectronic components and in particular for producing CT complexes which can be used for memory cells.

The invention provides new materials which can be used as a basis of memory elements and in particular memory elements having a size of a few nanometers, specifically: charge transfer complexes which comprise an electron donor selected from the group consisting of the compounds of the general formulae I or II and an electron acceptor selected from the group consisting of C20-C1000 fullerenes, and/or the compounds of the general formulae III and IV. A combination of a plurality of electron donors and a plurality of electron acceptors is also possible.

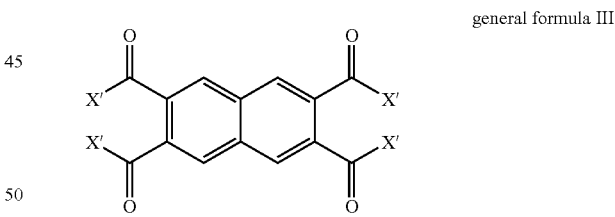

general formula III where X' is OR or $N(R)_2$ or two radicals X' are —NR—, and R is an alkyl group having 1-10 carbon atoms;

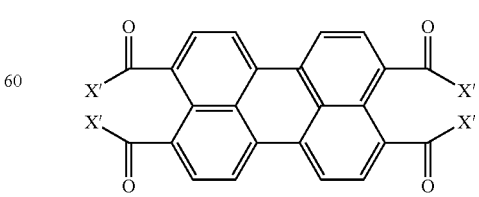

general formula IV and X' is as defined above.

Particularly preferred compounds of the general formula III are derivatives of naphthalenetetracarboxylic acid and in particular derivatives which can be prepared from the (readily available) 1,4,5,8-tetracarboxylic dianhydride. Reaction of the 1,4,5,8-tetracarboxylic dianhydride with alcohols or amines enables, for example, esters or imide or amide derivatives to be prepared. Particular preference is given to imide derivatives which can be obtained by reaction with primary alkylamines such as hexylamine or octylamine.

Particularly preferred compounds of the general formula IV are derivatives of the 3,4,9,10-tetracarboxylic acid, e.g. derivatives which can be prepared by reaction of the 3,4,9,10-tetracarboxylic anhydride with alcohols or primary alkylamines (e.g. hexylamine or octylamine).

Fullerenes are likewise readily available.

In a particular embodiment of the invention, the charge transfer complex comprises an electron donor selected from the group consisting of the compounds of the general formula 1 and fullerenes. Particular preference is given to charge transfer complexes with the compounds of the general formula 1 in which X=S. The charge transfer complexes comprising cyclic oligothiophenes and fullerenes having 60 or 70 carbon atoms have been found to be particularly useful.

Non-volatile memory cells which can be scaled down to a size of a few nanometers can be produced using the above-described charge transfer complexes.

The complexes according to the invention which are located between the anode and the cathode have a certain conductivity even in the ground state. The conductivity of the complexes according to the invention can be explained by the shift of the electron density from electron donors to the electron acceptors. In the ground state, the charge transfer complexes therefore comprise a partially positively charged electron donor molecule and a partially negatively charged electron acceptor molecule. The partial electron transfer in the ground state can be represented by the following formula:

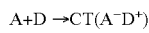

where $CT(A^-D^+)$ denotes a charge transfer complex in which the donor is only partially positively charged and the acceptor is only partially negatively charged.

The complex according to the invention also has a state of increased conductivity. This state can be explained by reduction or oxidation of the CT complex. In the reduction, an electron is injected by the cathode into the lowest unoccupied molecular orbital (LUMO) of the CT complex. The electron then exits again at the anode. In another mechanism, a hole is injected into the highest occupied molecular orbital (HOMO) (an electron is abstracted). The hole then exits again at the cathode. Ground state and state having an increased conductivity (due to transfer of a hole or an electron) are separated by a potential barrier. The hysteresis produced in this way can be utilized very well for information storage purposes.

DETAILED DESCRIPTION

Figure 1:
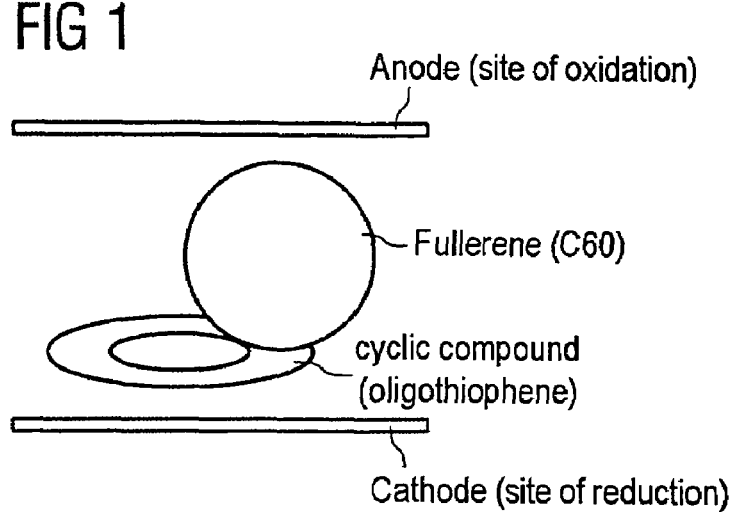
FIG. 1 schematically shows a memory cell according to the invention.

FIG. 1 schematically shows the memory cell of the invention for the example of a charge transfer complex comprising a polythiophene or oligothiophene molecule and a fullerene molecule as an active memory unit. The thiophene unit here constitutes the electron donor, and the fullerene unit constitutes the acceptor. The charge transfer complex comprising fullerene and thiophene is present between two electrodes. The complex can be reduced at the cathode and, depending on the conduction mechanism, an electron enters the complex or a hole leaves it. In contrast thereto, an electron leaves the complex or a hole enters it at the anode.

Figure 2:
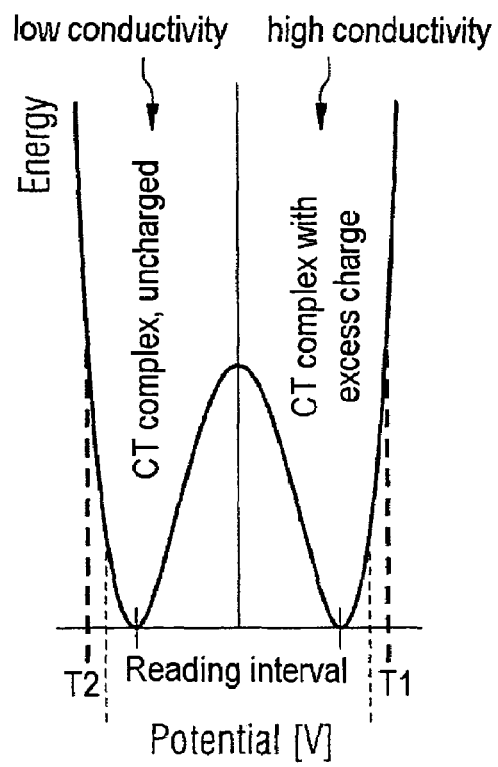
FIG. 2 shows the conductivity of the complex as a function of the applied potential.

The manner in which the memory functions can be seen from FIG. 2. The $CT(D^+A^-)$ complex (DAC) has a certain basic conductivity in the uncharged ground state at a given potential. Charge injection and/or charge extraction are balanced. If the potential is increased above a particular threshold T1, one of the processes dominates; for example, charge injection dominates. Depending on the charge carriers, a $DAC^+$ or $DAC^-$ radical cation or anion is then present averaged over time. The conductivity of this species is significantly higher than that of the uncharged DAC. $DAC^+$ or $DAC^-$ drops into the local minimum below T1. If the potential is decreased below T2, the initial state of the uncharged DAC is reestablished. In a reading range between T1 and T2, the memory cell can be read in a trouble-free manner as long as the reading voltage is not close to the switching limit. In addition, the memory is not volatile, since both the ground state and the state of increased conductivity are stable. If the structure is asymmetric, the arrangement can have diode character.

Figure 3:
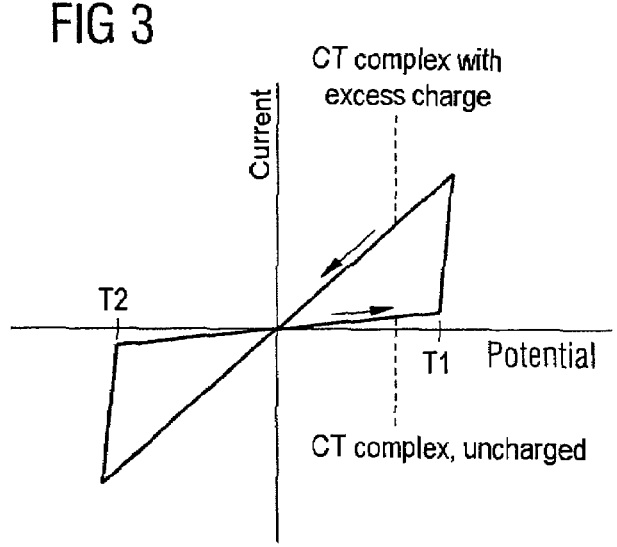
FIG. 3 schematically shows the current-potential curve of a memory element according to the invention.

FIG. 3 schematically shows a current-potential curve between the state of low conductivity and the state of higher conductivity. It is notable that the complex has an extraordinary stability, so that the measurements were able to be carried out under normal conditions and no particular measures, e.g. carrying out the measurements under inert gas conditions, were necessary.

Figure 4:
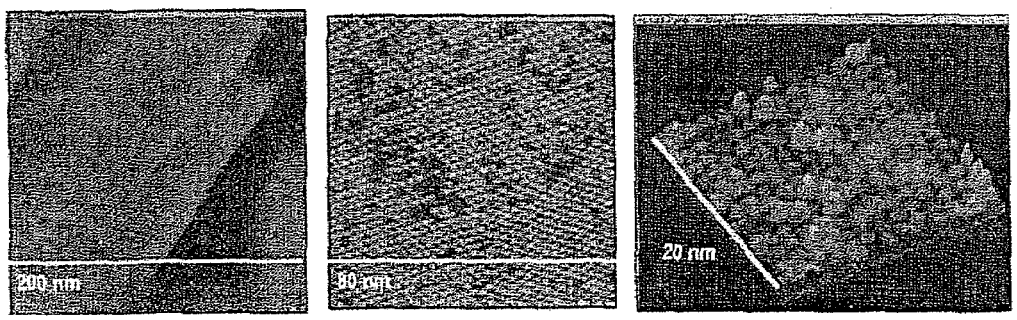
FIG. 4 shows a scanning tunnel micrograph (STM) of a CT complex comprising a cyclooligothiophene and a fullerene.

The complex according to the invention can be produced on a substrate of, for example, highly orientated pyrolithic graphite (HOPG), gold or other metals. The micrographs shown in FIG. 4 are micrographs of the complex according to the invention on HOPG. The applied bias on HOPG was in the range from −500 mV to −700 mV relative to the STM tip to achieve a tunnel current in the range 10-60 pA. In the ground state, the fullerene part already has a negative charge while the thiophene part is positively charged. The donor-acceptor complex is converted into a radical cation by injection of a hole into the fullerene part and in this state displays increased conductivity. Electrons are subsequently supplied by the graphite surface.

Figure 5:
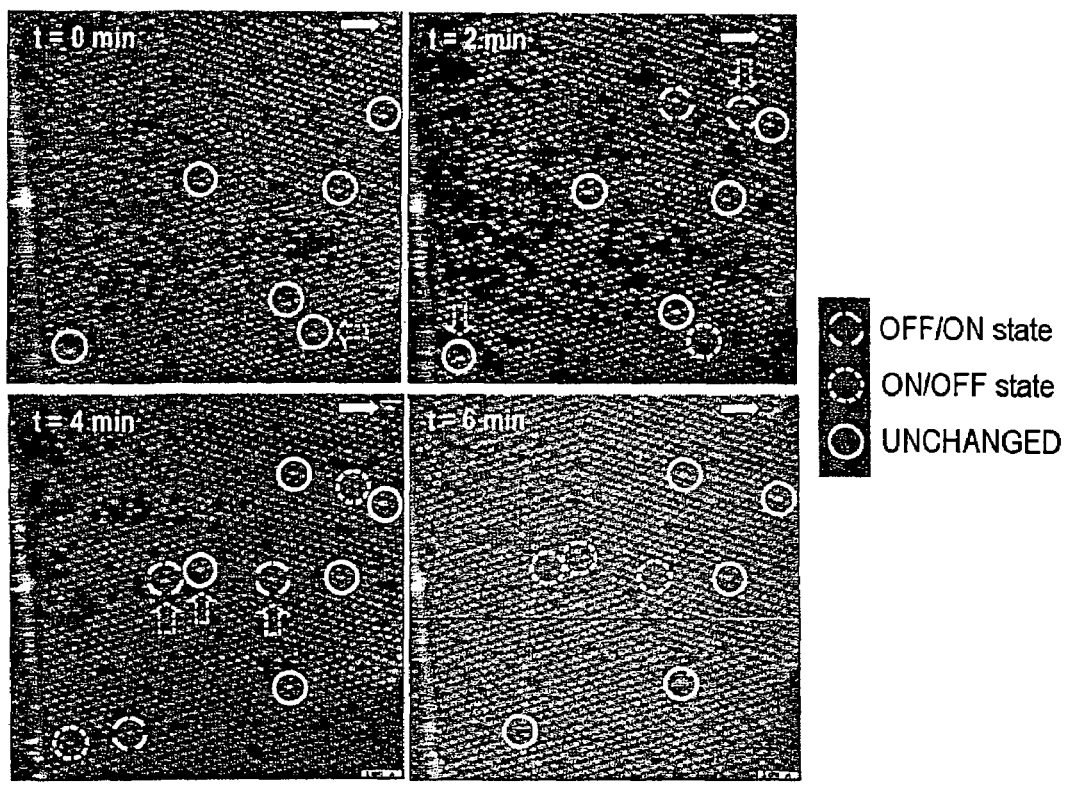
FIG. 5 shows the retention behavior of the complex according to the invention.

FIG. 5 depicts the retention behavior. The time between the micrographs was in each case 2 minutes. The complexes switch randomly on a time scale of a number of minutes. The dark points correspond to the state of low conductivity, while the light points correspond to the state of increased conductivity. The state of low conductivity is referred to as the "OFF" state and the state of increased conductivity is referred to as the "ON" state. The full circles indicate the unaltered CT complexes, the dotted circles indicate the complexes which transform from the "ON" state to the "OFF" state and the broken circles indicate complexes which transform from the "OFF" state to the "ON" state. In the initial state at t=O, six CT complexes are in the "ON" state while all others are in the "OFF" state.

At t=2 min, the CT complexes marked by broken circles are switched by the measurement conditions from OFF to ON, and the CT complex at bottom right was switched from ON to OFF (marked by a dotted circle).

At t=4, the CT complexes marked by broken circles change their state from OFF to ON. The CT complexes marked by dotted circles change their state from ON to OFF.

Although the complexes marked by a continuous circle displayed switching behavior, they did not change their state over a period of two minutes.

At t=6, the complexes marked by a dotted circle changed their state from ON to OFF. It is found that the three right-hand CT complexes have not changed their state as a result of the measurement conditions during the observation time.

Figure 6:
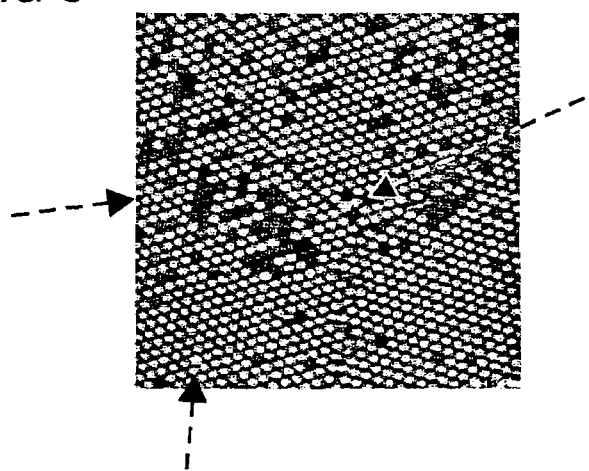
FIG. 6 shows the three switched complexes at a higher magnification.

FIG. 6 depicts the three switched complexes at a higher magnification.

The images shown in FIGS. 4 to 6 were produced using the CT complex of cyclo[12]thiophene and C60 fullerene. To prepare this complex, 0.1 mg of cyclo[12]thiophene solution (1) were dissolved in 10 ml of 1,2,4-trichlorobenzene. In an analogous way, 0.04 mg of C60 were dissolved in 10 ml of 1,2,4-trichlorobenzene (solution 2).

The monolayers were deposited on HOPG. For this purpose, the graphite surface was firstly scanned with a Pt/Ir STM tip. The parameters set (tunnel approach) form the basis for the imaging of the deposited cyclo[12]thiophene/fullerene layer. A few drops of solution 1 are subsequently applied to HOPG. As the solvent slowly evaporates over a number of hours, the thiophene monolayer is formed. After the solvent has evaporated in air at room temperature, solution 2 is applied.

The memory cell of the invention is suitable as a multibit memory cell, since a plurality of states having different conductivities can be produced.

A thiophene molecule can transfer a plurality of electrons to the fullerene units, so that a multibit state can be produced.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

What is claimed is:

1. A resistive memory cell comprising a compound of the formula I general formula I

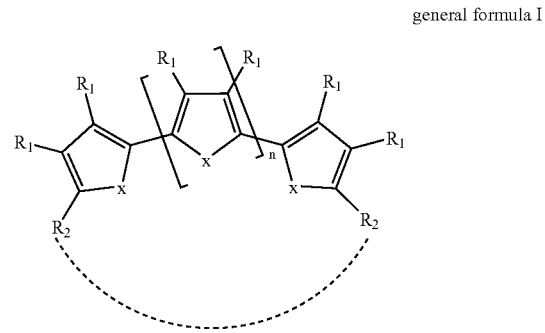

where:
n=1-100;
$R_2$ represents a chemical bond such that the compound of formula I forms a ring;
X=S; and
the radicals $R_1$ are each, independently of one another, H or a linear or branched alkyl chain which has from 1-10 carbon atoms or heteroatoms.

2. The resistive memory cell according to claim 1, wherein n=6-30.

3. The resistive memory cell according to claim 1, wherein $R_1$ is C1-C4-alkyl group.

4. The resistive memory cell according to claim 3, wherein $R_1$ is t-butyl or i-propyl.

* * * * *